United States Patent [19]

Watts et al.

[11] Patent Number: 6,027,691
[45] Date of Patent: Feb. 22, 2000

[54] AUTOMATIC CHEMISTRY ANALYZER

[75] Inventors: Richard P. Watts, Diamond Bar; David L. Goodale, Yorba Linda; Dang M. Ngo, Fountain Valley; Songai Tu, Yorba Linda; Michael Tran, Aliso Viejo; Michael L. Bell, Fullerton, all of Calif.

[73] Assignee: Beckman Coulter, Inc., Fullerton, Calif.

[21] Appl. No.: 09/133,927

[22] Filed: Aug. 13, 1998

Related U.S. Application Data

[62] Division of application No. 08/674,781, Jul. 3, 1996, Pat. No. 5,807,523.

[51] Int. Cl.$^7$ .................................................. G01N 35/02
[52] U.S. Cl. ................................ 422/64; 422/67; 436/43; 436/47; 436/48
[58] Field of Search .............................. 422/63, 64, 67, 422/100, 81, 102, 103, 104; 436/43, 47, 49, 50, 164, 172, 174, 179, 180; 366/168.1

[56] References Cited

U.S. PATENT DOCUMENTS

| | | |
|---|---|---|
| 4,298,570 | 11/1981 | Lillig et al. . |
| 4,539,296 | 9/1985 | Manabe . |
| 4,855,110 | 8/1989 | Marker et al. . |
| 5,169,602 | 12/1992 | Pang et al. . |
| 5,183,638 | 2/1993 | Wakatake . |
| 5,296,195 | 3/1994 | Pang et al. . |
| 5,356,525 | 10/1994 | Goodale et al. . |
| 5,365,798 | 11/1994 | Kressirer . |
| 5,424,212 | 6/1995 | Pinsi-Ober et al. . |

FOREIGN PATENT DOCUMENTS

| | | |
|---|---|---|
| 57182653 | 10/1982 | European Pat. Off. . |
| 289789A1 | 9/1988 | European Pat. Off. . |
| 520304A2 | 6/1991 | European Pat. Off. . |
| 569851A1 | 5/1992 | European Pat. Off. . |
| 2655426 | 4/1990 | France . |
| WO9320444 | 3/1993 | WIPO . |

*Primary Examiner*—Long V. Le
*Attorney, Agent, or Firm*—William H. May; Margaret A. Kivinski; Sheldon & Mak

[57] ABSTRACT

An automatic chemistry analyzer is provided having a high throughput and a high reliability. The analyzer uses nephelometric and turbimetric analyzers to analyze a wide variety of parameters within liquid samples typically generated in, for example, a large medical testing laboratory. The machine employs a unique probe and stirring rod assembly mounted at a slight angle with one another using rack and pinion assemblies so that the lower end of the probe and the lower end of the stirring rod are in very close proximity to one another. This feature allows the machine to be used in unusually small reaction cuvettes. The analysis machine also includes an onboard control sample so that the machine can be programmed to periodically calibrate its analyzing equipment during the course of normal operation. The machine also includes a sample station carousel having retainer clips for retaining a sample container rack which is constructed to retain a bar-coded card containing information regarding reagents used in the machine. A bar code reader located proximate to the sample carousel reads the bar-coded reagent information into the controller.

15 Claims, 11 Drawing Sheets

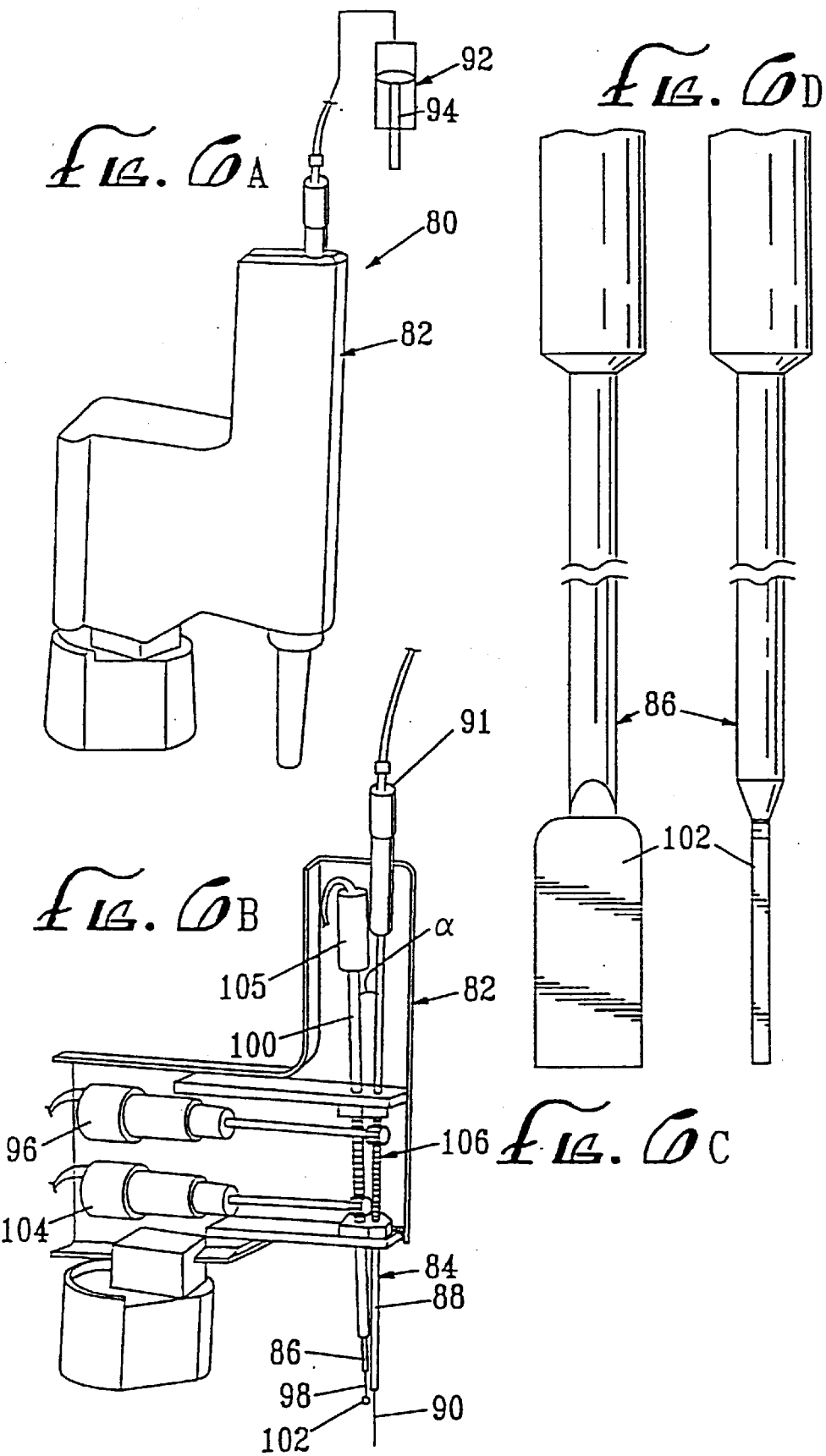

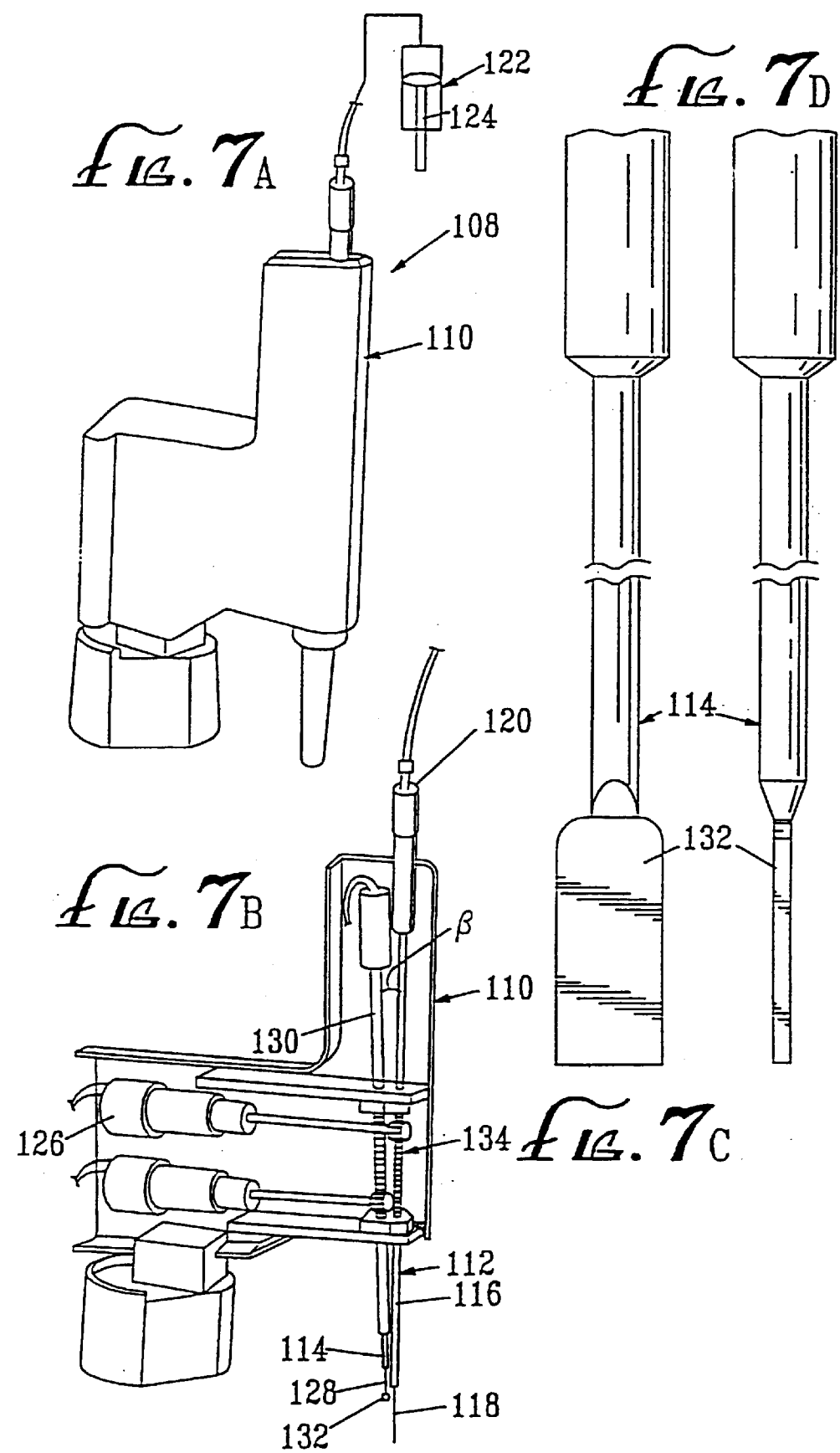

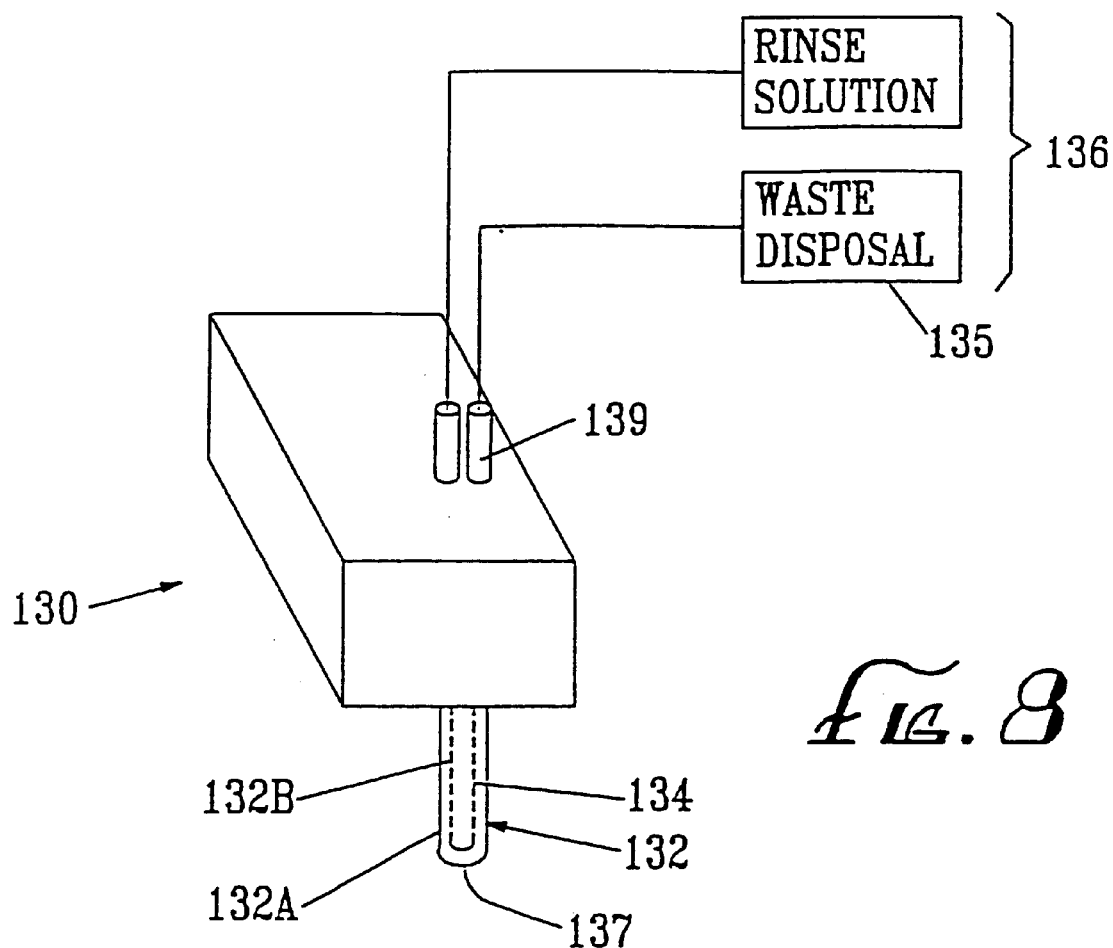

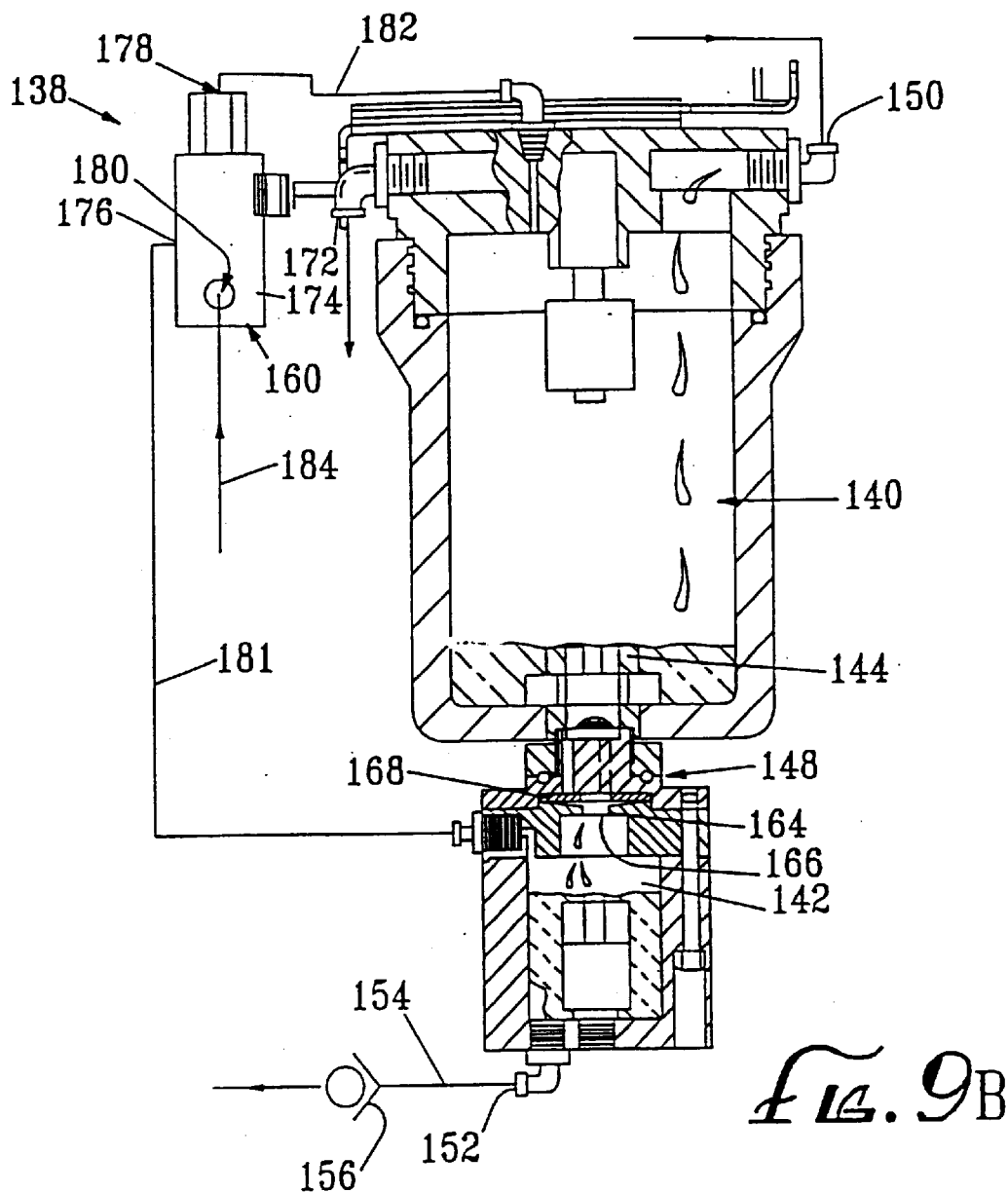
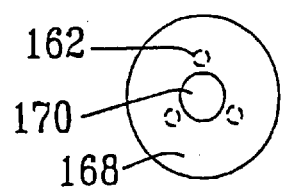
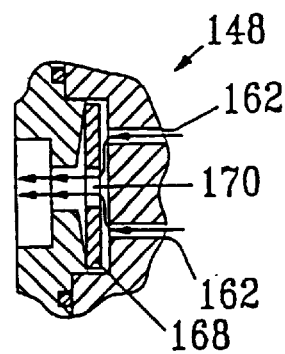

AUTOMATIC CHEMISTRY ANALYZER

This is a division of the application Ser. No. 08/674,781, filed Jul. 3, 1996 now U.S. Pat. No. 5,807,523.

FIELD OF THE INVENTION

This invention generally relates to the field of automated clinical chemical analyzers, and specifically to compact automated chemical analyzers using a nephelometer.

BACKGROUND OF THE INVENTION

A number of different automated clinical chemical analyzers are known in the art. Such analyzers range from simple, largely manually-operated instruments to highly complex, nearly fully automated instruments. Each analyzer has its own particular performance characteristics related to the number of different tests ("menu") that the analyzer can perform and the number of samples that the analyzer can process in a given period of time ("throughput").

As sophisticated and efficient as are many of today's automated analyzers, several problems continue to exist. First and foremost is throughput capacity. Every second which can be saved in the analysis time of a single sample means millions of dollars in savings of precious medical resources. Therefore, there is continuous pressure on analyzer manufacturers to increase throughput. The automated analyzers of the prior art are quite fast, but not fast enough.

An additional problem in the prior art is cost of operation. Most automated analyzers of the prior art use relatively large reaction containers ("cuvettes") which require an excessive amount of expensive reagent materials.

Still another problem in the prior art is the amount of time that an operator must spend inputting data and instructions into the analyzer. This diminishes throughput and causes excessive manpower expenses.

Still another problem related to throughput is the necessity of prior art analyzing machines which use a nephelometric analyzer to periodically shut down operations to calibrate the nephelometer.

Finally, there is a problem regarding throughput vacuum drain systems used in automatic analyzers of the prior art. Such vacuum drain systems are generally wasteful with respect to the use of vacuum. Such waste results in the use of excessively large vacuum usage and may decrease throughput of the analyzer.

Accordingly, there is a need for an automated clinical chemical analyzer which has greater throughput than prior art analyzer modules, requires less manpower to operate, is more reliable and is more efficient.

SUMMARY OF THE INVENTION

The invention satisfies these needs. The invention is a device for determining at least one parameter of a liquid sample comprising:

(a) a body;

(b) a motorized sample station disposed within the body, the sample station being sized and dimensioned to retain a plurality of sample containers and having a sample extraction site, the sample station being movable within the body such that, when the sample station retains a plurality of sample containers, individual sample containers can alternatively be moved to and away from the sample extraction site;

(c) a motorized reagent station disposed within the body, the reagent station being sized and dimensioned to retain a plurality of reagent containers and having a reagent extraction site, the reagent station being movable within the body such that, when the reagent station retains a plurality of reagent containers, individual reagent containers can alternatively be moved to and away from the reagent extraction site;

(d) a motorized random access analyzing station disposed within the body, the random access analyzing station being sized and dimensioned to retain a plurality of cuvettes and having a cuvette mixing site, a cuvette washing site, a random access analyzing station analyzing site and an analyzer disposed proximate to the random access analyzing station analyzing site for determining at least one parameter of a sample disposed within the cuvettes, the random access analyzing station being movable within the body such that, when the random access analyzing station retains a plurality of cuvettes, individual cuvettes can alternatively be moved to and away from (1) the cuvette mixing site, (2) the cuvette washing site and (3) the random access analyzing station analyzing site;

(e) a sample probe arm assembly attached to the body, the sample probe arm assembly including (1) a sample probe arm, (2) a hollow sample probe having an internal chamber, an open lower end and an open upper end and (3) an elongate rotatable sample stirring rod having a lower end and an upper end, the lower end of the sample stirring rod including a sample stirring rod paddle attached thereto, the sample probe and the sample stirring rod being disposed generally vertically in close proximity to one another, the sample probe being vertically movable between a lower sample probe position and an upper sample probe position, the sample stirring rod being movable of the sample probe between a lower sample stirring position and an upper sample stirring rod position, the sample probe and sample stirring rod being disposed within the sample probe arm assembly such that, when the sample probe is at the lower sample probe position and the sample stirring rod is at the lower sample stirring rod position, the sample probe arm being movable between a first sample probe arm position wherein the sample probe is immediately above the sample extraction site and a second sample probe arm position wherein the sample probe is immediately above the cuvette mixing site;

(f) a sample probe positioning motor for moving the sample probe between the lower sample probe position and the upper sample probe position;

(g) a sample stirring rod positioning motor for moving the sample stirring rod between the lower sample stirring rod position and the upper sample stirring rod position;

(h) a sample stirring rod rotating motor for rotating the sample stirring rod;

(i) a sample probe pressure altering assembly for alternatively applying a positive pressure and a negative pressure to the interior chamber of the sample probe;

(j) a reagent probe arm assembly attached to the body, the reagent probe arm assembly including (1) a reagent probe arm, (2) a hollow reagent probe having an internal chamber, an open lower end and an open upper end and (3) an elongate rotatable reagent stirring rod having a lower end and an upper end, the lower end of the reagent stirring rod including a reagent stirring rod paddle attached thereto, the reagent probe and the reagent stirring rod being disposed generally vertically in close proximity to one another, the reagent probe being vertically movable between a lower reagent probe position and an upper reagent probe position, the reagent stirring rod being movable of the reagent probe between a lower reagent stirring rod position and an upper reagent stirring rod position, the reagent probe and reagent stirring rod being disposed within the reagent probe arm assembly such that, when the reagent probe is at the lower reagent probe position and the reagent stirring rod is at the lower reagent stirring rod position, the reagent probe arm being movable between a first reagent probe arm position wherein the reagent probe is immediately above the reagent extraction site and a second reagent probe arm position wherein the reagent probe is immediately above the cuvette mixing site;

(k) a reagent probe positioning motor for moving the reagent probe between the lower reagent probe position and the upper reagent probe position;

(l) a reagent stirring rod positioning motor for moving the reagent stirring rod between the lower reagent stirring rod position and the upper reagent stirring rod position;

(m) a reagent stirring rod rotating motor for rotating the reagent stirring rod;

(n) a reagent probe pressure altering assembly for alternatively applying a positive pressure and a negative pressure to the interior chamber of the reagent probe;

(o) a cuvette wash station attached to the body, the cuvette wash station including at least one motorized hollow cuvette wash station probe having an internal chamber, an open lower end and an open upper end, the cuvette wash station being disposed such that the cuvette wash station probe is immediately above the cuvette washing site; and (p) a cuvette wash station probe supply and disposal assembly for alternatively (1) providing pressurized washing liquid from a source of washing liquid to the cuvette wash station probe for washing a cuvette disposed within the random access analyzing station at the cuvette washing site and (2) providing a negative pressure to the interior chamber of the cuvette wash station probe for removing waste liquids from a cuvette disposed within the random access analyzing station at the analyzing site and for transferring such waste liquids to a suitable disposal site.

Preferably, on each probe arm the distance between the probe and the stirring rod at their respective lowermost positions is between about 1.7 and about 5.3 mm, more preferably between about 1.7 and about 3.5 mm, most preferably between about 1.7 and about 3 mm.

Also, it is preferably that on each probe arm, the probe and the stirring rod be vertically movable independently of one another.

Preferably, each probe and stirring rod are attached to their probe arm by a rack and pinion assembly for raising and lowering the probe and stirring rods. This feature allows for independent operation of the probe and stirring rod while providing that the lower tip of the probe and stirring rod (at their lowermost positions) are very close to one another. This, in turn, allows the use of smaller reaction containers requiring a minimum of expensive reagents.

In a preferred embodiment, the sample station comprises a rotating sample carousel having an exterior wall with a retainer assembly for retaining a card displaying bar-coded information on the exterior wall. This allows a bar code reader disposed within the device to read bar-coded information regarding the reagent containers used in the device.

In another preferred embodiment, the sample station comprises a plurality of dilution sections, each having a plurality of dilution cups. This feature allows the device to minimize the use of expensive reagents.

In still another preferred embodiment, the cuvette wash probe supply and disposal assembly includes a waste trap assembly comprising (a) a waste trap reservoir, (b) a waste collector bowl disposed below the waste trap reservoir, (c) a vertically disposed connector conduit for connecting the waste trap reservoir in fluid communication with the waste collector bowl, the connector conduit having an uppermost lip over which waste liquids within the waste trap reservoir can spill over into the waste collector bowl, (d) a connector conduit check valve for preventing the upward flow of liquids and pressurized air within the connector conduit from the waste collector bowl to the waste trap reservoir, (e) an inlet port in the upper portion of the waste trap reservoir for receiving waste liquid from the cuvette wash station probe, (f) an outlet port in the bottom of the waste collector bowl for draining liquid within the waste collector bowl to a suitable waste disposal facility via a drain conduit, (g) a drain conduit check valve disposed within the drain conduit to prevent liquids to flow into the waste collector bowl via the drain conduit, (h) a level sensor for sensing the level of liquid within the waste collector bowl and emitting a corresponding level sensor signal, (i) a switch assembly for alternatively applying pressure and vacuum to the waste collector bowl, (j) a waste trap controller for receiving the level sensor signal from the level sensor and therewith controlling the switching assembly to allow the application of vacuum and pressure to the waste collector bowl in such a way that (i) when the level of liquid within the waste collector is below a preselected set point, vacuum is applied to the waste collector bowl to draw waste liquid from the waste trap reservoir and (ii) when the level of liquid within the waste collector is at the preselected set point, pressure is applied to the waste collector bowl to blow down waste liquid within the waste collector bowl to the drain conduit.

The invention is also a method for analyzing a plurality of liquid samples using the device described above.

The invention is also a chemical test reagent kit for use in an automated testing machine having an internal bar code reader. The kit comprises at least one container containing reagent and a bar code card containing bar coded information regarding the reagent. The bar code card is sized and dimensioned to be read by the internal bar code reader of an automated testing machine.

The invention provides significant improvements over the prior art by reducing reagent costs and operating expenses while increasing throughput, accuracy and reliability.

DESCRIPTION OF THE DRAWINGS

These and other features, aspects and advantages of the present invention will become better understood with reference to the following description, appended claims and accompanying drawings where:

FIG. 6A is a perspective view of a sample probe arm assembly having features of the invention;

FIG. 6B is a cut-away view of the sample probe arm assembly shown in FIG. 6A;

FIG. 6C is a front view of a sample stirring rod useful in the invention;

FIG. 6D is a side view of the sample stirring rod shown in FIG. 6C;

FIG. 7A is a perspective view of a reagent probe arm assembly having features of the invention;

FIG. 7B is a cut-away view of the reagent probe arm assembly shown in FIG. 7A;

FIG. 7C is a front view of a reagent stirring rod useful in the invention;

FIG. 7D is a side view of the reagent stirring rod shown in FIG. 7C;

FIG. 8 is a perspective view of a cuvette wash station useful in the invention;

FIG. 9B is a cross-sectional view of the fully assembled waste trap assembly shown in FIG. 9A;

FIG. 9C is a cross-sectional side detail view of a valve useful in the waste trap assembly shown in FIGS. 9A and 9B;

FIG. 9D is a plan view of a flexible desk useful in the waste trap assembly shown in FIGS. 9A–9C.

DETAILED DESCRIPTION OF THE INVENTION

The following discussion describes in detail one embodiment of the invention and several variations of that embodiment. This discussion should not be construed, however, as limiting the invention to those particular embodiments. Practitioners skilled in the art will recognize numerous other embodiments as well. For a definition of the complete scope of the invention, the reader is directed to the appended claims.

Figure 1:
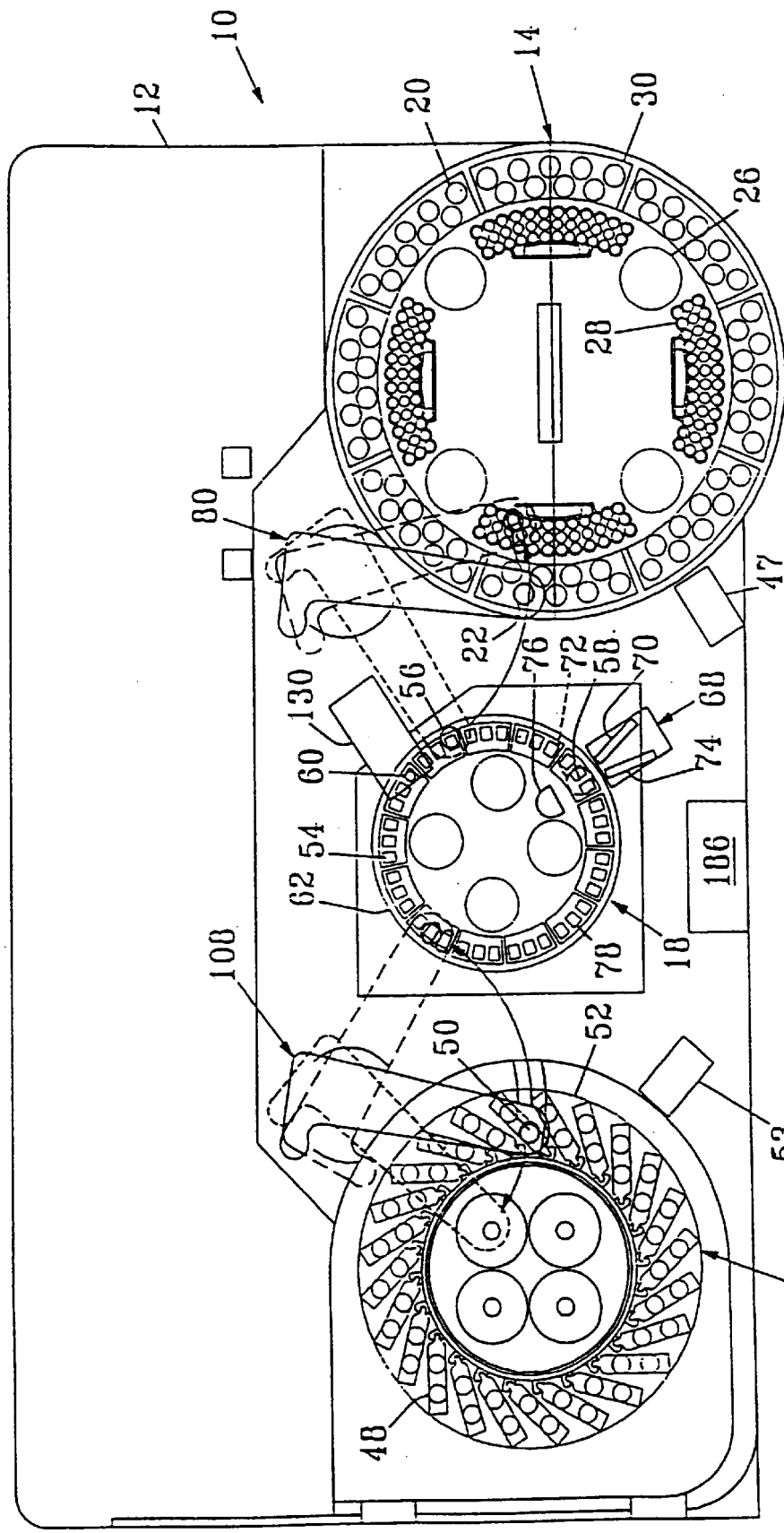
FIG. 1 is a schematic plan view of an automated analyzing machine having features of the invention.
Figure 2:
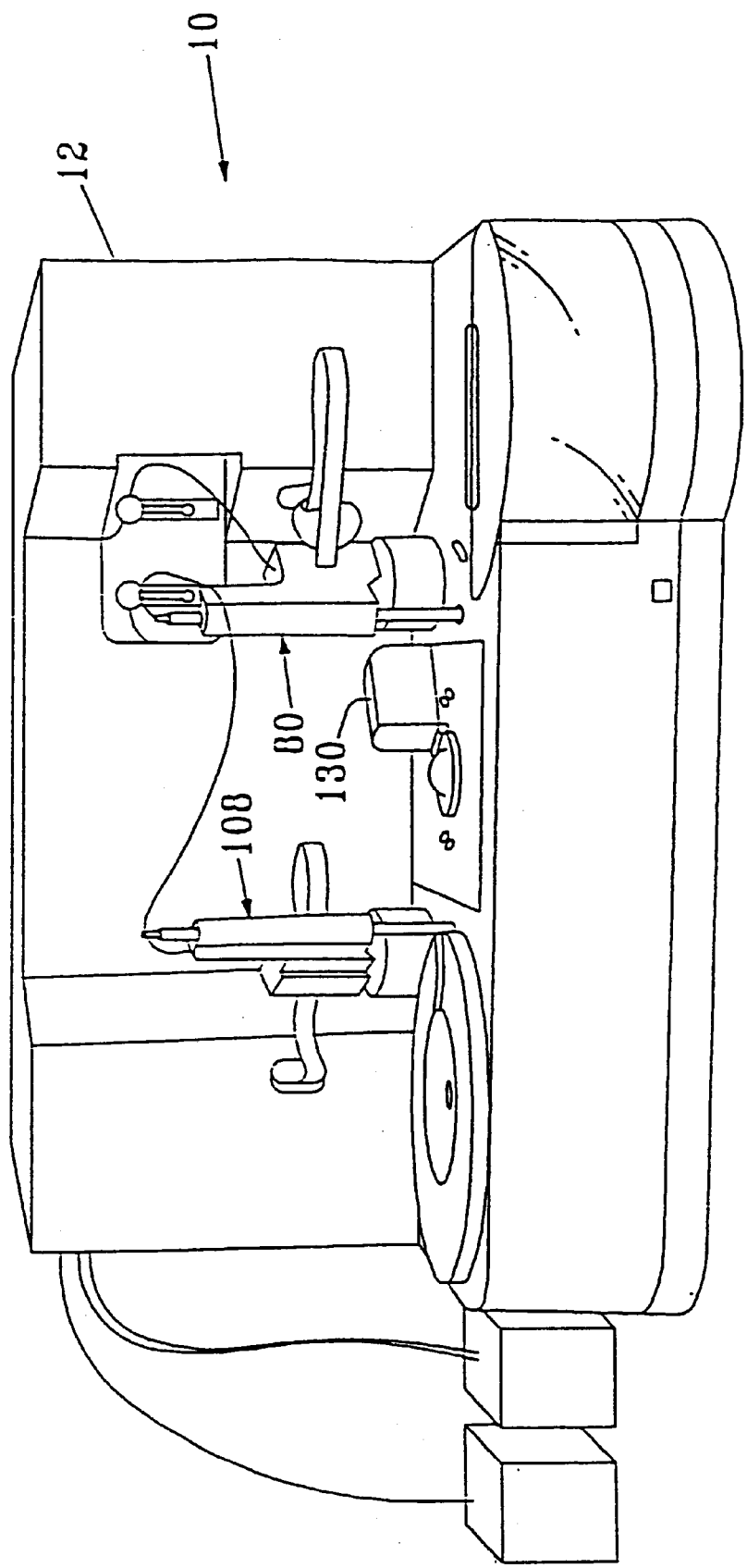
FIG. 2 is a front view of an automated analyzing machine having features of the invention.

FIGS. 1 and 2 show an automated analyzing machine 10 having features of the invention. The machine 10 comprises a body 12, a sample station 14, a reagent station 16 and a random access analyzing station 18.

The body 12 is generally a cabinet providing a housing for the various operative components used in the analyzing machine 10. The body 12 is typically made from a lightweight metal such as a lightweight sheet steel. The body 12 can include a canopy (not shown) for fully enclosing the operative components of the machine 10.

The sample station 14 is sized and dimensioned to retain a plurality of sample containers 20. The sample station 14 has at least one sample extraction site 22.

Figure 3:
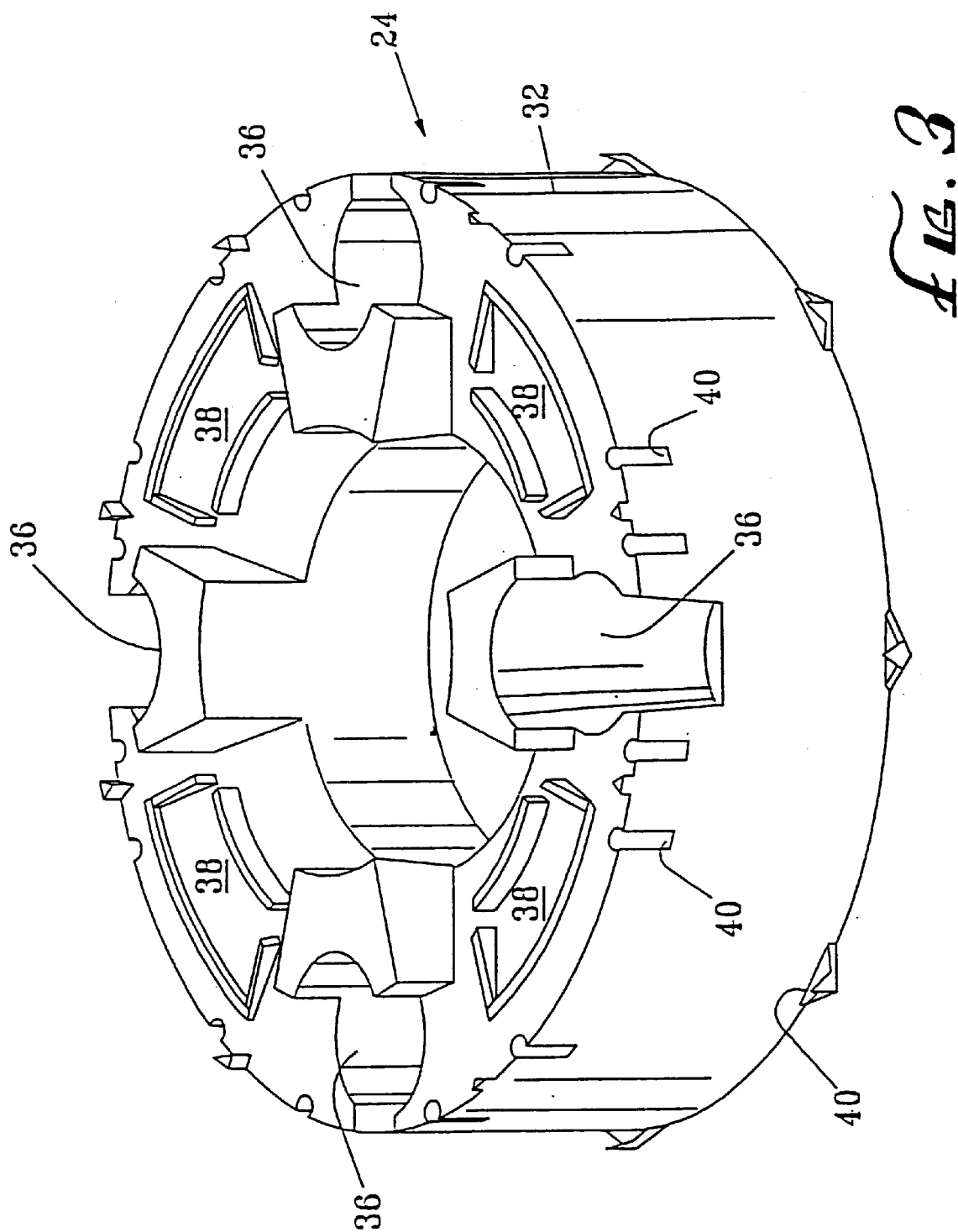
FIG. 3 is a perspective view of a sample carousel having features of the invention.

The sample station 14 preferably comprises a revolving sample carousel 24 as illustrated in FIG. 3. Typically, the sample carousel 24 is made from a lightweight metal or molded plastic. The sample carousel 24 is preferably sized and dimensioned to retain a plurality of sample containers 20, one or more diluent containers 26, and a plurality of dilution sections 28.

In the embodiment shown in the drawings, the sample carousel 24 comprises a carousel retainer assembly 40 for retaining a sample container rack 30 on the exterior wall 32 of the sample carousel 24. Such retainer assembly 40 can be slots as shown in the embodiment illustrated in the drawings.

Figure 10:
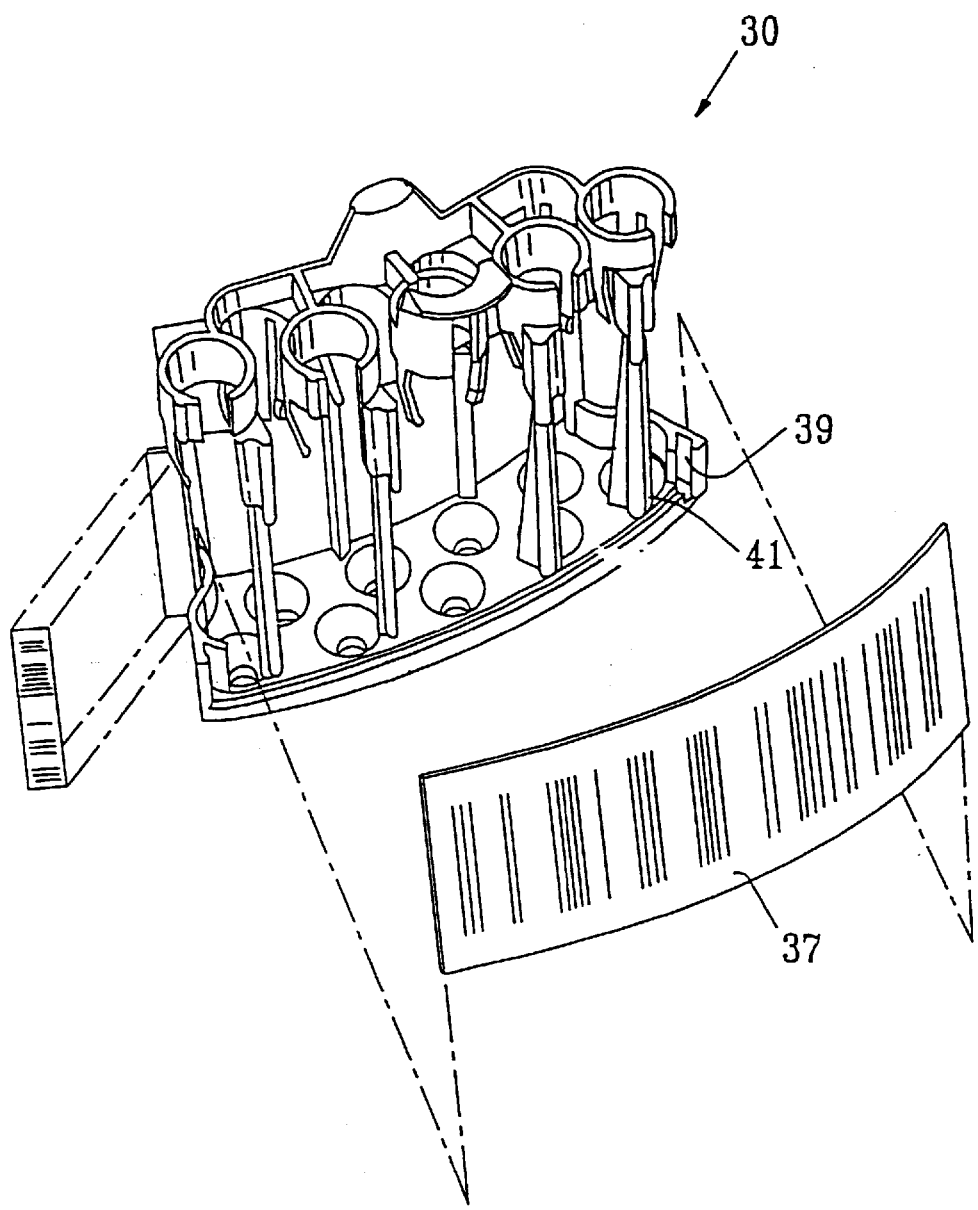
FIG. 10 is a perspective view of a sample container rack having features of the invention.

The sample rack 30 preferably comprises a sample container rack retainer assembly 39 for retaining a card 37 displaying bar-coded information on the forward portion 41 of the sample container rack 30. Such sample container rack retainer assembly 39 can be resilient clips as shown in the embodiment illustrated in FIG. 10. However, many other ways of attaching the bar-coded card 37 to the forward portion 41 of the sample container rack 30 can also be used as well, including clamps, clips, prongs, snaps, buttons, hook and loop fasteners, pins, etc. It is preferable that the sample container rack retainer assembly 39 allows the operator to quickly and easily attach and later de-attach a bar code card 37 from the forward portion 41 of the sample container rack 30, most preferably without the use of tools.

In this embodiment, each sample container rack 30 houses nine individual sample containers 20 in a generally upright disposition.

Figure 4A:
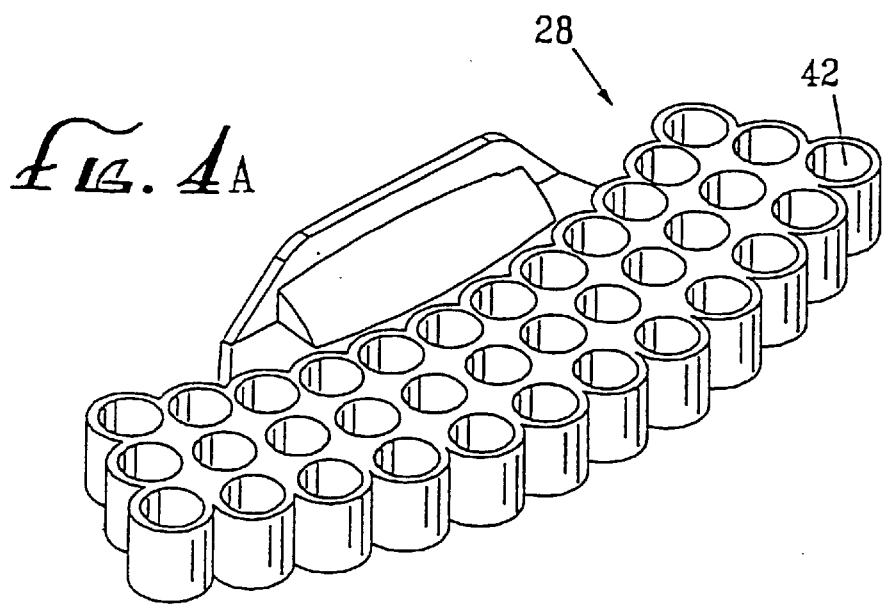
FIG. 4A is a perspective view of a dilution section having features of the invention.
Figure 4C:
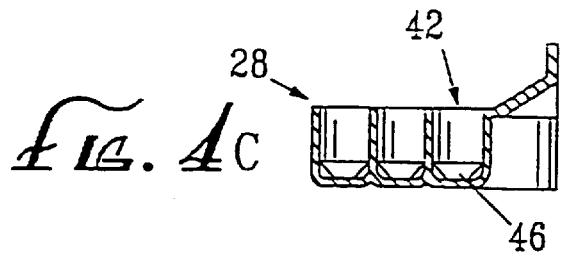
FIG. 4C is a cross-sectional side view of the dilution section shown in FIG. 4B, taken along line 4C—4C.
Figure 4B:
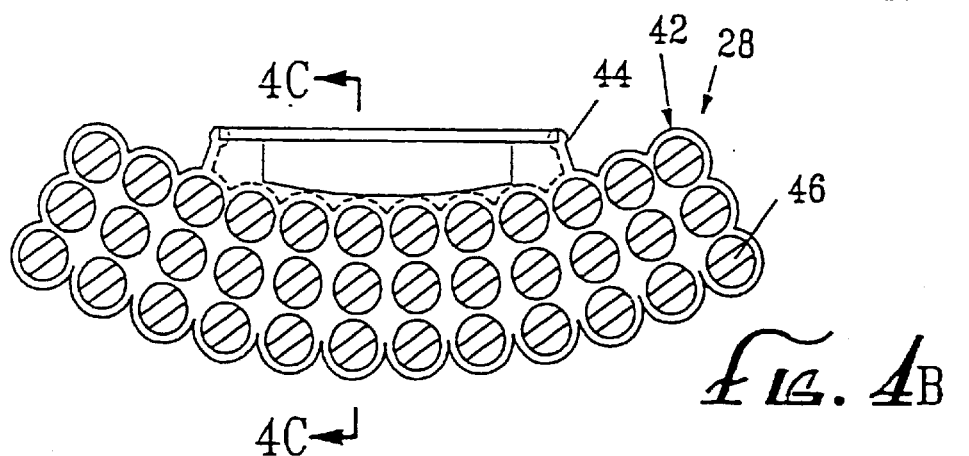
FIG. 4B is a plan view of the dilution section of FIG. 4A.
Figure 4D:
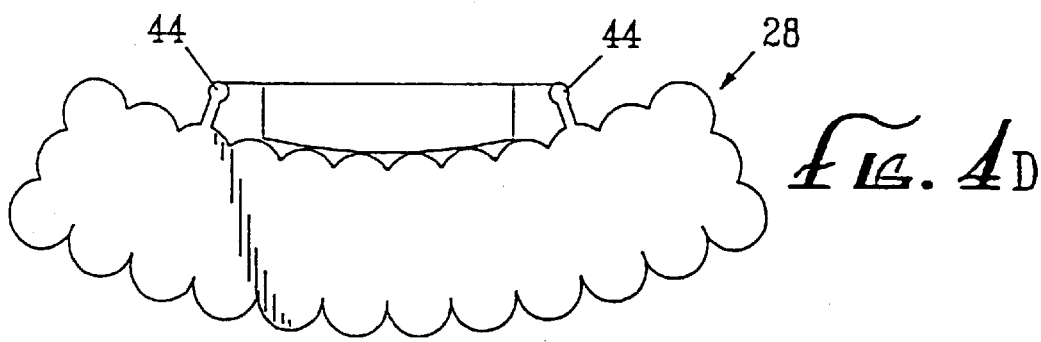
FIG. 4D is a bottom side view of the dilution container shown in FIGS. 4A–4C.

The sample carousel 24 shown in FIG. 3 has four diluent container retention locations 36 and four dilution section retention locations 38. The dilution sections 28 each comprise a plurality of dilution cups 42 as shown in FIGS. 4A–4C. Typically, each dilution section 28 is made from a molded plastic. Preferably, each dilution section 28 is easily installed and removed from the sample carousel 24 for ease of cleaning. It is also preferable that the dilution sections 28 be easily and quickly installed into and deinstalled from the sample carousel 24 without use of tools. The embodiment shown in the drawings has resilient nodes 44 which allow the dilution sections 28 to snap fit in the dilution section retention locations 38.

Each dilution cup 42 holds between about 0.01 and about 1.0 milliliters of liquid. As shown in FIG. 4C, each dilution cup 42 is tapered at the bottom to form a dilution cup narrow well 46 so that small amounts of liquid within the dilution cup 42 puddle within the narrow well and thereby remain easily extractable from the dilution cup 42. Each dilution cup narrow well 46 typically can retain between about 10 microliters and about 100 microliters. This feature minimizes reagent waste. This feature is especially important where the dilution cups 42 are made from a plastic material which is hydrophobic. In such cases, small amounts of liquid within the dilution cups 42 tend to bead instead of puddling, making it difficult to extract the liquid from the dilution cup 42.

The sample carousel 24 is movable by a rotating motor (not shown) such that each sample container 20 disposed on the sample carousel 24 can be alternatively positioned under and moved away from the one sample extraction site 22.

Preferably, the sample station 14 further comprises a sample station bar code reader 47 for reading bar-coded information on the sample containers 20 within the sample station 14 and/or on a bar code card 37 disposed on the forward portion 41 of the sample container rack 30.

The reagent station 16 is sized and dimensioned to retain a plurality of reagent containers 48 and has at least one reagent extraction site 50. A particularly useful reagent container 48 usable in the machine of the invention is described in detail in pending U.S. patent application Ser.

No. 08/675,586, entitled "Reagent Cartridge", which is filed contemporaneously herewith and which is also incorporated herein by reference in its entirety. The reagent station 16 is movable within the body such that individual reagent containers 48 disposed within the reagent station 16 can be alternatively moved to and away from the reagent extraction site 50.

Like the sample station 14, the reagent station 16 preferably comprises a rotatable reagent carousel 52, typically made from a lightweight metal or molded plastic. The reagent carousel 52 is rotated by a reagent station motor (not shown).

Preferably, the reagent station 16 is refrigerated, such as to a temperature of about 15° C. Such refrigeration preserves reagent life and minimizes reagent evaporation.

Preferably, the reagent station 16 further comprises a reagent station bar code reader 53 for reading bar-coded information on reagent containers 20 within the reagent station 16 and/or on the exterior of the reagent carousel 24.

The random access analyzing station 18 is sized and dimensioned to retain a plurality of reaction cuvettes 54 of the type commonly known in the nephelometric and turbimetric arts. The random access analyzing station 18 comprises at least one cuvette mixing site 56, one random access analyzing station analyzing site 58 and a cuvette washing site 60.

Like the sample station 14 and the reagent station 16, the random access analyzing station 18 preferably comprises a rotatable carousel 62 which is rotated by a random access analyzing station motor (not shown).

Figure 5A:
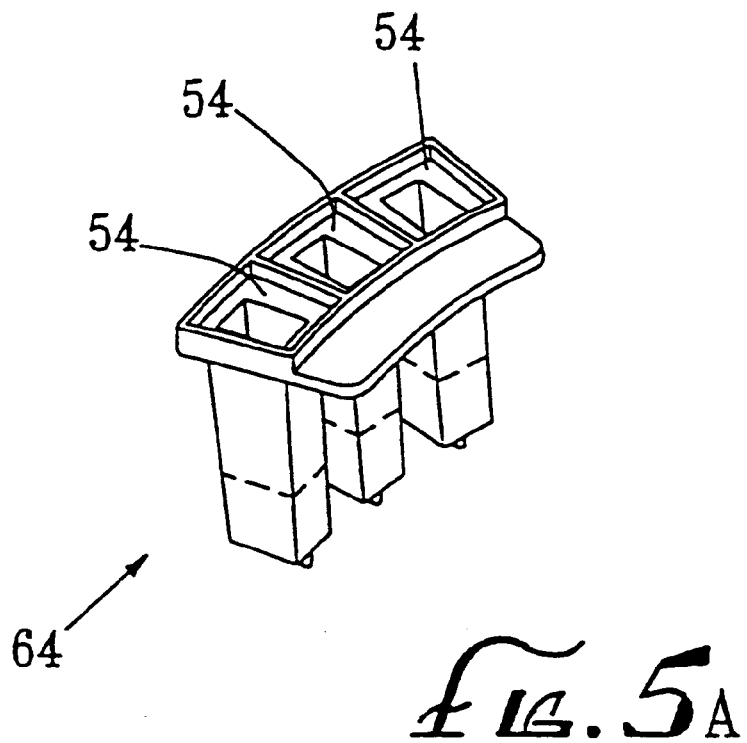
FIG. 5A is a perspective view of a reaction cuvette module useful in the invention.
Figure 5B:
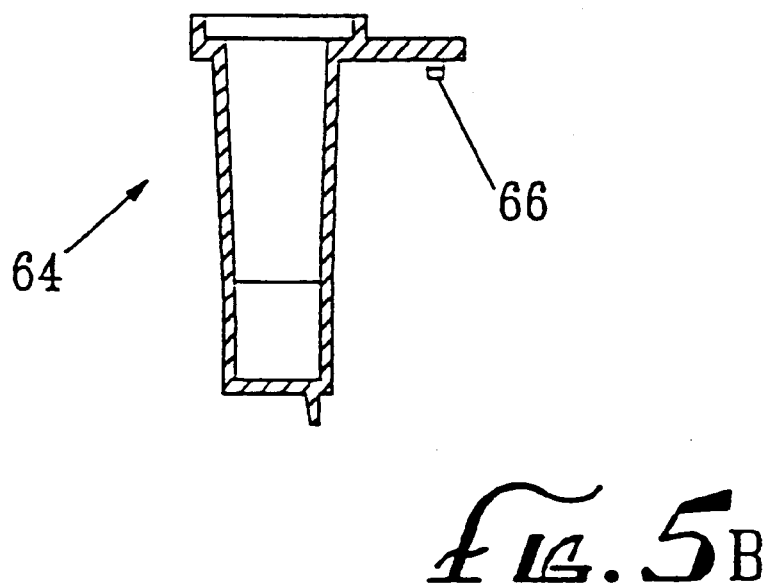
FIG. 5B is a cross-sectional side view of the reaction cuvette module shown in FIG. 5A.
Figure 9A:
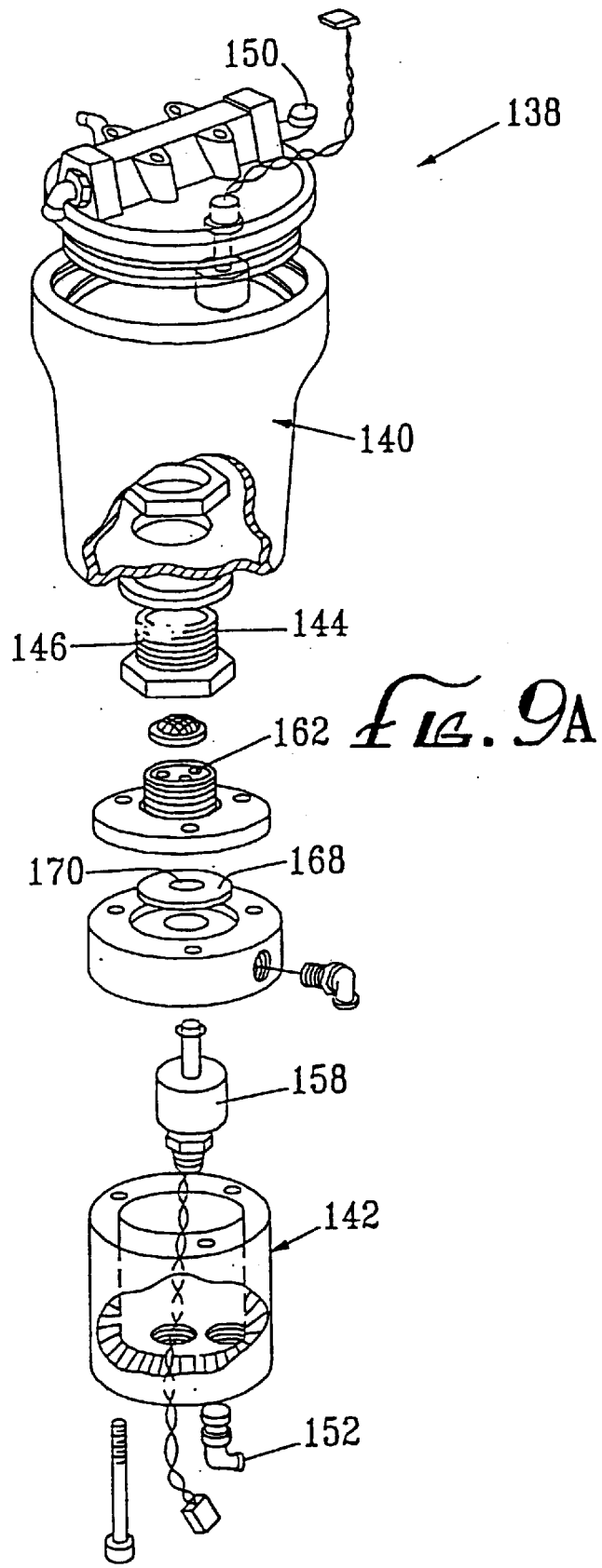
FIG. 9A is an exploded view of a waste trap assembly having features of the invention.

In the embodiment shown in the drawings, the reaction cuvettes 54 are disposed in cuvette modules 64, each cuvette module 64 containing three individual cuvettes 54. The cuvette modules 64 are shown in FIGS. 5A and 5B. Each cuvette module 64 has prongs 66 to facilitate firm attachment to the random access analyzing station carousel 62. To minimize the cost of expensive reagent, it is important that the cuvettes 54 be made as small as practically possible.

In most applications, it is preferable that the random access analyzing station 18 be operatable at a fixed elevated temperature, such as about 37° C. To accomplish this, the random access analyzing station 18 preferably includes means for circulating heated air upwardly through the random access analyzing station 18.

The random access analyzing station 18 further comprises a random access analyzing station analyzer 68 which is disposed proximate to the random access analyzing station analyzing site 58 for determining at least one parameter of a sample disposed within a cuvette 54 within the random access analyzing station 18. In a preferred embodiment, the random access analyzing station analyzer 68 is a nephelometer and turbidimeter combination. Such a combination is well-known in the art. A detailed description of a typical nephelometer and turbidimeter combination is set forth, for example, U.S. Pat. No. 5,296,195, which is incorporated herein by reference in its entirety. A particularly useful nephelometer and turbidimeter combination useful in the analysis machine of the invention is described in pending U.S. patent application Ser. No. 08/674,780, entitled "Nephelometer and Turbidimeter Combination", which is filed contemporaneously herewith and which is incorporated herein by reference in its entirety.

In a typical nephelometer and turbidimeter combination, there is a first light source 70 disposed proximate to the random access analyzing station analyzing site 58 for directing a first beam of light through a cuvette 54 disposed at the random access analyzing site 58 to a first light receptor 72. In a preferred embodiment, this first light source 70 is a visible diode laser emitting light at a wave length between about 600 and about 850 nm. Preferably, a second light source 74 is also disposed proximate to the random access analyzing station analyzing site 58 for directing a second beam of light through a cuvette 54 disposed at the random access analyzing site 58 to a second light receptor 76. In a preferred embodiment, this second light source 74 is a light emitting diode capable of emitting light at a wave length between about 850 and about 1050 nm. Both first and second light receptors 72 and 76 measure the amount of scattered light as the first and second light beams 70 and 74 are projected through the cuvette 54. In the embodiment shown in FIG. 1, the first light receptor 72 is disposed below the reaction cuvette to measure the amount of light scattered at a 90° angle with respect to the first beam of light. As is well-known in the art, such scattering of light can be accurately correlated with one or more specific parameters of the liquid within the cuvette 54.

Preferably, the random access analyzing station 18 further comprises an onboard control sample 78. Such onboard control sample 78 allows the user to program the machine to automatically calibrate the random access analyzing station analyzer 68 during normal operation of the machine 10. This feature maximizes accuracy and reliability over similar machines of the prior art. This feature also increases throughput by eliminating the need to periodically shut down the machine 10 to calibrate the random access analyzing station analyzer 68. A particularly useful onboard control sample usable in the invention is described in detail in U.S. Pat. No. 5,741,441, entitled "Non-Liquid Scatter Standard", which is filed contemporaneously herewith and which is incorporated herein by reference in its entirety.

The onboard control sample comprises a non-evaporating calibration standard material. Preferably, such non-evaporating standardization material is a gel, such as a silicon gel described in U.S. Pat. No. 5,741,441. Preferably, the silicon gel has an index of refraction between about 1.3 and about 1.5 and includes an effective light scattering amount of inorganic particles suspended within the gel. The inorganic particles have an index of refraction greater than that of the silicon gel.

In one embodiment, the silicon gel is the result of a mixing and curing of a two-component system wherein one of the components comprises; (1) 83 to 98.6 parts by weight of a silanol endstopped diorganopolysiloxane polymer, wherein the organo groups are monovalent hydrocarbon radicals, and (2) 1.4 to 17 parts by weight of resinous copolymer comprising $R_3SiO_{0.5}$ units and $SiO_2$ units, wherein R is a monovalent hydrocarbon radical and wherein said copolymer has from about 0.5 to about 1 $R_3SiO_{0.5}$ unit per $SiO_2$ unit.

In a still sore preferred embodiment, one of the components of the two-component system has a composition comprising: (1) 10 to 50 parts by weight of an alkyl silicate of the formula:

$$(R^1)_m Si(OR^2)_{4-m}$$

and partial hydrolysis products thereof, wherein $R^1$ and $R^2$ are monovalent hydrocarbon radicals, m is 0 or 1 and which is pre-reacted with (2) an effective catalytic amount of curing catalyst, (3) 10 to 30 parts by weight of a self-bonding additive having the formula:

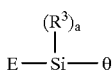

$$E\!-\!\underset{\underset{\displaystyle |}{}}{\overset{(R^3)_a}{Si}}\!-\!\theta \qquad (3\text{-a})$$

wherein $R^3$ is a monovalent hydrocarbon radical, E is a hydrolyzable group selected from the group consisting of alkoxy, phenoxy, amino and dialkylamino and θ is a nitrogen functional radical which is reacted with unsaturated or aromatic hydrocarbon residue, which in addition to nitrogen functionality may be functionalized by a radical selected from the group consisting of amino, cyano, thio, oxo and ester, and combinations thereof, and a is a number varying from 0 to 2, and (4) 10 to 40 parts by weight vinyl terminated linear diorganopolysiloxane fluid in a viscosity varying from 100 to 50,000 centipoise at 25° C., wherein the organo groups are monovalent hydrocarbon radicals.

The analysis machine 10 of the invention further comprises a sample probe arm assembly 80 such as shown in FIGS. 6A–6D. The sample probe arm assembly 80 includes a sample probe arm 82, a hollow sample probe 84 and a rotatable sample stirring rod 86. The sample probe 84 has an internal chamber 88, an open lower end 90 and an open upper end 91. A sample probe pressure altering assembly 92 is provided to alternatively place pressure or a vacuum on the internal chamber 88. Preferably, the pressure altering assembly 92 comprises a syringe 94.

The sample probe 84 is disposed generally vertically in the sample probe arm 82 and is movable by a sample probe motor 96 between a lower sample probe position and an upper sample probe position.

The sample stirring rod 86 has a lower end 98, an upper end 100 and a stirring rod paddle 102. The sample stirring rod 86 is also disposed generally vertically in the sample probe arm 82 and is movable by a sample stirring rod motor 104 between a lower sample stirring rod position and an upper sample stirring rod position. The sample stirring rod is operatively rotated by a sample stirring rod rotating motor 105.

Preferably, the raising and lowering of the sample stirring rod 86 is independent of the raising and lowering of the sample probe 84. This provides speed and flexibility over important similar devices in the prior art which can only raise and lower the stirring rod 86 at the same time that the probe 84 is raised and lowered.

Preferably, the sample stirring rod 86 and the sample probe arm 84 are both raised and lowered using a rack and pinion assembly 106. Such rack and pinion assembly 106 allows the sample probe 84 and the reagent probe 86 to be mounted close enough to one another to achieve the close proximities of their respective lower ends 90 and 98 described immediately below.

The sample probe 84 and the sample stirring rod 86 are disposed within the sample probe arm 82 at a slight angle with respect to one another. Preferably, this angle α is between about 2.4° and about 2.6°. The sample probe 84 and the sample stirring rod 86 are angled towards one another so that, when both the sample probe 84 and the sample stirring rod 86 are at their respective lower positions, the distance between the lower end 90 of the sample probe 84 and the lower end 98 of the sample stirring rod 86 is between about 1.7 mm and about 5.3 mm, more preferably between about 1.7 mm and about 3.5 mm, most preferably between about 1.7 mm and about 3 mm. By structuring the sample probe 84 and the sample stirring rod 86 so as to be so close to one another at their respective lower positions 90 and 98, the sample probe 84 and sample stirring rod 86 can effectively be used within reaction cuvettes 54 which are much smaller than those used in prior art analyzing machines. The ability to use such small reaction cuvettes 54 results in significant reagent savings to the operator. It also allows the operator to conduct clinical analyses with very small samples.

The device of the invention further comprises a reagent probe arm assembly 108 such as shown in FIGS. 7A–7D. The reagent probe arm assembly 108 includes a reagent probe arm 110, a hollow reagent probe 112 and a rotatable reagent stirring rod 114. The reagent probe 112 has an internal chamber 116, an opened lower end 118 and an open upper end 120. A reagent probe pressure altering assembly 122 is provided to alternatively place pressure or a vacuum on the internal chamber 116. Preferably, the pressure altering assembly comprises a syringe 124.

The reagent probe 112 is disposed generally vertically in the reagent probe arm 110 and is movable by a reagent probe motor 126 between a lower reagent probe position and an upper reagent probe position.

The reagent stirring rod 114 has a lower end 128, an upper end 130 and a stirring rod paddle 132. The reagent stirring rod 114 is also disposed generally vertically in the reagent probe arm 110 and is movable by a reagent stirring rod motor 132 be between a lower reagent stirring rod position and an upper reagent stirring rod position. As is the case with respect to the sample probe 84 and the sample stirring rod 86, it is preferable that the raising and lowering of the reagent stirring rod 114 be independent of the raising and lowering of the reagent probe 112.

It is also preferable that the reagent stirring rod 114 and the reagent probe 112 be raised and lowered using a rack and pinion assembly 134. Such rack and pinion assembly 134 allows the reagent probe 112 and the reagent stirring rod 114 to be mounted close enough to one another to achieve the close proximities at their lower ends 118 and 128 described immediately below.

Like the sample probe 84 and the sample stirring rod 86, the reagent probe 112 and reagent stirring rod 114 are disposed within the reagent probe arm 110 at a slight angle with respect to one another. Preferably, this angle β is between about 2.4° and about 2.6° The reagent probe 112 and the reagent stirring rod 114 are angled towards one another for the same reason that the sample probe 84 and the sample stirring rod 86 are angled towards one another: that is to provide for a convergence of the lower ends 118 and 128 of the reagent probe 112 and the reagent stirring rod 114 to a distance between about 1.7 mm and about 5.3 mm, more preferably between about 1.7 and about 3.5 mm, most preferably between about 1.7 and about 3 mm. This close proximity of the lower ends 118 and 128 of the reagent probe 112 and the reagent stirring rod 114 allow the use of very small reaction cuvettes 54.

Preferably, both the sample probe arm 82 and the reagent probe arm 108 comprise level controllers (not shown) for determining the elevation of the probes 84 and 112 and/or the stirring rods 86 and 114 relative to a liquid level.

The machine of the invention 10 further comprises a cuvette wash station 130 attached to the body. The cuvette wash station 130 includes at least one hollow cuvette wash station probe 132 having an internal chamber 134, an open lower end 136 and an open upper end 138. The cuvette wash station 130 is disposed such that the cuvette wash station probe 132 is immediately above the cuvette washing site 60.

The cuvette wash station probe 132 is movable by a cuvette wash station motor (not shown) between a lower cuvette wash station probe position and an upper cuvette wash station probe position.

In the embodiment shown in FIG. 8, the cuvette wash station probe 132 comprises two concentrically disposed cuvette wash station probes 132a and 132b. One probe 132 is used to evacuate the contents of a cuvette and transmit such contents to a suitable disposal site 135. The other probe 132 is used to provide the cuvette with a washing solution.

The device of the invention further comprises a cuvette wash station probe supply and disposal assembly 136 for alternatively (1) providing pressurized washing liquid from a source of washing liquid to the cuvette washing station probe 132 for washing a cuvette 54 disposed at the cuvette washing site 60 and (2) providing a negative pressure to the interior chamber 134 of the cuvette wash station probe 132 for removing waste liquids from a cuvette 54 disposed within analyzing site 60 and for transferring such waste liquids to a suitable disposal site 135.

A preferred wash station probe supply and disposal assembly 136 comprises a waste trap assembly 138 shown in FIGS. 9A–9D. The waste trap assembly 138 comprises a waste trap reservoir 140 and a waste collector bowl 142 disposed below the waste trap reservoir 140. A vertically disposed connector conduit 144 connects the waste trap reservoir 140 in fluid communication with the waste collector bowl 142. The connector conduit 144 has an uppermost lip 146 over which waste liquids which collect within the waste trap reservoir 140 spill over into the waste collector bowl 142. The connector conduit 144 has a connector conduit check valve 148 for preventing the upward flow of liquids and pressurized air within the connector conduit 144 from the waste collector bowl 142 to the waste trap reservoir 140.

The waste trap reservoir 140 has an inlet port 150 in the upper portion of the waste trap reservoir 140 for receiving waste liquid from the cuvette wash station 130. The waste collector bowl 142 has an outlet port 152 in the bottom of the waste collector bowl 142 for draining liquid within the waste collector bowl 142 to a suitable waste disposal facility via a drain conduit 154. The drain conduit 154 has a drain conduit check valve 156 to prevent liquids from flowing back into the waste collector bowl 142 via the drain conduit 154.

A level sensor 158 is disposed within the waste collector bowl 142 for sensing the level of liquids within the waste collector bowl 142 and emitting a corresponding level sensor signal. In operation, the waste trap reservoir 140 is operatively connected to a source of vacuum. Also, the waste collector bowl 142 is operatively connected via a switch 160 to a source of vacuum and to a source of pressurized air.

The waste trap assembly 138 further comprises a waste trap controller (not shown) for receiving the level sensor 158 signal from the level sensor and using that signal to control the application of a vacuum and pressure to the waste collector bowl in the following way: (i) when the level of liquid within the waste collector bowl 142 is below a preselected set point, vacuum is applied to the waste collector bowl 142 to draw waste liquid from the waste trap reservoir 140 and (ii) when the level of liquid within the waste collector bowl 142 is at the preselected set point, pressure is applied to the waste collector bowl 142 to blow down waste liquid within the waste collector bowl 142 to the drain conduit 154.

The waste trap assembly connector conduit check valve 148 preferably comprises an inlet conduit 162, a valve seat 164 disposed within the inlet conduit 162 and in fluid tight communication therewith, an outlet conduit 166 disposed below the valve seat 164 and in fluid tight communication therewith and a plug 168 loosely disposed within the valve seat 164 such that (1) when the pressure within the inlet conduit is equal to or greater than the pressure within the outlet conduit 166, the plug 168 is not held tightly against the valve seat 164 so as to allow liquid waste within the inlet conduit 162 to gravitate into the outlet conduit 166 and (2) when the pressure within the inlet conduit 162 is less than the pressure within the outlet conduit 166, the plug 168 is held tightly against the valve seat 164 so as to prevent liquid waste within the inlet conduit 162 from gravitating into the outlet conduit 166 and to prevent pressurized air in the outlet conduit 166 from flowing through the inlet conduit 164 into the waste trap reservoir 140.

Preferably, the plug 168 is a flexible disk as shown in the drawings. The flexible disk has at least one central aperture 170 which is off-set from the inlet conduit 162.

Preferably, the waste trap 138 assembly further comprises (a) a vacuum source inlet port 172 disposed in the waste trap reservoir 140, the vacuum source inlet port 172 being connectable to a source of vacuum, (b) a three way valve 174 having a common port 176, a normally open port 178 and a normally closed port 180, (c) a first pressure source conduit 181 connected in fluid tight communication between the common port 176 and the waste collection bowl 142, (d) a second pressure source conduit 182 connected in fluid tight communication between the normally open port 178 and the waste trap reservoir 140, and (e) a third pressure source conduit 184 connected in fluid tight communication between the normally closed port 180 and a source of air pressure.

This waste trap assembly 138 provides significant advantages over prior art waste trap assemblies. The waste trap assembly 138 of the invention requires only one vacuum storage reservoir 140 and one vacuum pump. Moreover, a wash cycle need not be interrupted for liquid waste evacuations. Also, no external waste pump is required as is generally required by prior art systems. This is because the waste trap assembly 138 of the invention relies on air pressure to drive the waste out of the assembly. Some prior art systems also use pressurized air to force waste out of a waste trap assembly. However, such systems are wasteful of vacuum since each time the reservoir level signals for the three-way valve to switch, the entire vacuum contents of the reservoir are replaced by pressurized air to force waste to the pump. This can significantly slow down operation of the machine since replenishing the vacuum can take 16 seconds and more. Moreover, a relatively large vacuum pump is required.

Preferably, the analyzing machine 10 of the invention further comprises a controller 186 for controlling the operation of the motors, analyzers and bar code readers. Preferably, the controller 186 includes a digital computer which is also programmed to receive the results from the analyzer 68 and report those results to the operator in an efficient format.

In operation, the operator of a preferred embodiment of the analysis machine loads the reagent station 16 with premixed reagent from a kit. The kit includes one or more reagent containers 48 containing premixed reagent and a bar code card having bar-coded information thereon regarding the reagent within the kit.

After loading the reagent containers 48 into the reagent station 16, the operator places the bar-coded card 37 from the reagent kit on the forward portion 41 of the sample container rack 30 using the sample container rack retainer assembly 40. The operator instructs the sample station bar code reader 47 to read into the controller the bar-coded information contained on the bar-coded card 37. The operator then removes the bar-coded card 37 from the sample container 30.

The operator then loads the sample carousel 24 with sample containers 20 containing samples to be analyzed. The sample containers 20 are loaded into sample container racks 30 and the sample container racks 30 are attached to the exterior perimeter of the sample carousel 24. A label containing bar-coded information regarding the identity of each of the samples and the analyses to be run on each of the samples is attached to each sample container 20. The operator then places diluent containers 26 in the sample carousel 24 and places clean dilution sections 28 in the sample carousel 24. The operator then engages the machine 10 which carries out the following steps automatically.

The sample carousel 24 is rotated, making frequent stops. Whenever a container 20 is disposed in front of the sample station bar code reader 47, the bar code reader 47 reads the bar-coded information on the label on the sample container and passes that information along to the controller 186.

The sample probe arm 82 moves the sample station probe 84 to a position immediately above the sample extraction site 22. The sample probe 84 is lowered from its upper probe position until the sample probe level controller senses the fact that the sample probe 84 is below the surface of the sample within the sample container 20 positioned at the sample extraction site 22.

The sample probe pressure altering assembly 92 is then caused to draw a vacuum in the sample probe internal chamber 88. This, in turn, causes sample within the sample container 20 to be drawn into the sample probe internal chamber 88. The sample probe 84 is then raised to its upper position and the sample probe arm 82 rotates to a position over one of the dilution cups 42. The sample probe 84 is again lowered into the dilution cup 42 and the sample probe pressure altering assembly 92 causes the sample within the sample probe 84 to be discharged into the dilution cup 42.

The sample probe arm 82 then rotates the sample probe 84 to a position immediately above one of the diluent containers 26 in the sample station 14. The sample probe 84 is lowered from its upper position to a position below the surface of the diluent in the diluent container 26 as sensed by the sample probe level controller. The pressure altering assembly 92 causes a vacuum to be drawn within the sample probe internal chamber 88 and diluent is drawn into the sample probe 84. The sample probe 84 is then raised to its upper position and the sample arm rotates the sample probe 84 to a position immediately above one of the dilution cups 42. The sample probe 84 is lowered into the dilution cup 42 and the pressure altering assembly 92 pressures the diluent out of the sample probe 84 and into the dilution cup 42.

The sample stirring rod 86 is then lowered into the dilution cup 42 and the sample stirring rod rotating motor 105 is engaged to mix the sample and the diluent.

Next, the sample probe 84 is again lowered into the dilution cup 42 and the diluent-sample mixture is drawn into the sample probe 84. The sample probe arm 82 then rotates the sample probe 84 to a position immediately above the cuvette 54 at the cuvette mixing site 56, the sample probe 84 is lowered into the cuvette 54, and the diluent-sample mixture is expelled from the sample probe 84 into the cuvette 54 by the sample probe pressure altering means 92.

Immediately before or after these steps, the controller 186 causes the reagent probe arm 110 to maneuver immediately above the appropriate reagent container 48 within the reagent extraction site 22 and the reagent probe 112 is lowered into the reagent container 48 and a quantity of reagent is drawn into the reagent probe 112. The reagent probe 112 is then raised to its upper position and the reagent arm 110 rotates the reagent probe 112 over the cuvette 54 at the cuvette mixing site 56. The reagent probe 112 is then lowered into the cuvette 54 and the reagent is discharged into the cuvette 54.

At this point, either the sample stirring rod 86 (or the reagent stirring rod 114 depending upon which stirring rod is immediately above the cuvette mixing site at this point in time) is lowered into the cuvette 54 and the rotating motor is engaged to agitate the reagent-sample mixture with the stirring rod paddle 102. After mixing, the stirring rod 86 is retracted to its upper position.

The controller 186 then causes the random access analyzing station carousel 62 to rotate the cuvette 54 having the reagent-sample mixture past the random access analyzing station analyzing site 58. At this analyzing site 58, the random access analyzing station analyzer 68 analyzes the contents of the cuvette 54 and transmits that information to the controller 186. Preferably, the controller 186 causes the cuvette 54 to pass through the random access analyzing station analyzing site 58 on numerous occasions and instructs the analyzer 68 to analyze the contents on each of those numerous occasions. By making numerous analyses of the same reagent-sample mixture, the results ultimately reportable by the controller 186 are therefore very precise in nature.

After the contents of the cuvette 54 are analyzed, the random access analyzer carousel 62 is rotated so that the cuvette 54 is immediately below the cuvette washing site 60. At the cuvette washing site 60, the cuvette wash station probe 132 is lowered into the cuvette 54 and the contents of the cuvette 54 are extracted out of the cuvette 54 and sent to suitable disposal using the cuvette wash probe supply and disposal assembly 136. The cuvette 54 is then washed with pressurized washing liquid and that liquid is also sent to disposal using the cuvette wash probe supply and disposal assembly 136. The cuvette 54 is then clean and ready for another analysis operation.

The controller 186 is preferably programmed to keep track of a large number of reaction cuvettes 54 in various stages of the analysis process. The controller 186 causes the random access analyzing station carousel 62 to rotate with great rapidity, moving any of the large number of active cuvettes 54 to the various cuvette sites for one or more of the various operations described above. In this way, the analyzing machine 10 can carry out a large number of analyses in a very small amount of time.

Periodically during normal operation of the machine, the controller 186 causes the random access analyzing station analyzer 68 to analyze the contents of the onboard control sample 78. If the results of this analysis suggests that the analyzer 68 is out of calibration, the analyzer 68 is automatically recalibrated.

The invention provides significant improvements over the prior art by reducing reagent costs and operating expenses while increasing throughput, accuracy and reliability.

Although the present invention has been described in considerable detail with reference to certain preferred versions thereof, other versions are possible. Therefore, the spirit and scope of the appended claims should not be limited to the description of the preferred versions contained herein.

What is claimed is:

1. A device for determining at least one parameter of a liquid sample, the device comprising:
   (a) a body;
   (b) a motorized sample station disposed within the body, the sample station being sized and dimensioned to retain a plurality of sample containers and having a sample extraction site, the sample station being movable within the body such that, when the sample station retains a plurality of sample containers, individual sample containers can alternatively be moved to and away from the sample extraction site;

(c) a motorized reagent station disposed within the body, the reagent station being sized and dimensioned to retain a plurality of reagent containers and having a reagent extraction site, the reagent station being movable within the body such that, when the reagent station retains a plurality of reagent containers, individual reagent containers can alternatively be moved to and away from the reagent extraction site;

(d) a motorized random access analyzing station disposed within the body, the random access analyzing station being sized and dimensioned to retain a plurality of cuvettes and having at least one cuvette mixing site, a cuvette washing site, a random access analyzing station analyzing site and an analyzer disposed proximate to the random access analyzing station analyzing site for determining at least one parameter of a sample disposed within the cuvettes, the random access analyzing station further comprising an onboard control sample, the onboard control sample comprising a non-evaporating calibration standard material, the random access analyzing station being movable within the body such that (i) the onboard control sample can be moved to and away from the random access analyzing station analyzing site, and (ii), when the random access analyzing station retains a plurality of cuvettes, individual cuvettes can alternatively be moved to and away from (1) the cuvette mixing site, (2) the cuvette washing site and (3) the random access analyzing station analyzing site;

(e) a sample probe arm assembly attached to the body, the sample probe arm assembly including (1) a sample probe arm, (2) a hollow sample probe having an internal chamber, an open lower end and an open upper end and (3) an elongate rotatable sample stirring rod having a lower end and an upper end, the lower end of the sample stirring rod including a sample stirring rod paddle attached thereto, the sample probe and the sample stirring rod being disposed generally vertically in close proximity to one another, the sample probe being vertically movable between a lower sample probe position and an upper sample probe position, the sample stirring rod being movable independent of the sample probe between a lower sample stirring rod position and an upper sample stirring rod position, the sample probe arm being movable between a first sample probe arm position wherein the sample probe is immediately above the sample extraction site and a second sample probe arm position wherein the sample probe is immediately above the at least one cuvette mixing site;

(f) a sample probe arm motor for moving the sample probe arm between the first sample probe arm position and the second sample probe arm position;

(g) a sample probe positioning rotor for moving the sample probe between the lower sample probe position and the upper sample probe position;

(h) a sample stirring rod positioning motor for moving the sample stirring rod between the lower sample stirring rod position and the upper sample stirring rod position;

(i) a sample stirring rod rotating motor for rotating the sample stirring rod;

(j) a sample probe pressure altering assembly for alternatively applying a positive pressure and a negative pressure to the interior chamber of the sample probe;

(k) a reagent probe arm assembly attached to the body, the reagent probe arm assembly including (1) a reagent probe arm, (2) a hollow reagent probe having an internal chamber, an open lower end and an open upper end and (3) an elongate rotatable reagent stirring rod having a lower end and an upper end, the lower end of the reagent stirring rod including a reagent stirring rod paddle attached thereto, the reagent probe and the reagent stirring rod being disposed generally vertically in close proximity to one another, the reagent probe being vertically movable between a lower reagent probe position and an upper reagent probe position, the reagent stirring rod being movable independent of the reagent probe between a lower reagent stirring rod position and an upper reagent stirring rod position, the reagent probe arm being movable between a first reagent probe arm position wherein the reagent probe is immediately above the reagent extraction site and a second reagent probe arm position wherein the reagent probe is immediately above the at least one cuvette mixing site;

(l) a reagent probe arm motor for moving the reagent probe arm between the first reagent probe arm position and the second reagent probe arm position;

(m) a reagent probe positioning motor for moving the reagent probe between the lower reagent probe position and the upper reagent probe position;

(n) a reagent stirring rod positioning motor for moving the reagent stirring rod between the lower reagent stirring rod position and the upper reagent stirring rod position;

(o) a reagent stirring rod rotating motor for rotating the reagent stirring rod;

(p) a reagent probe pressure altering assembly for alternatively applying a positive pressure and a negative pressure to the interior chamber of the reagent probe;

(q) a cuvette wash station attached to the body, the cuvette wash station including a hollow cuvette wash station probe having an internal chamber, an open lower end and an open upper end, the cuvette wash station probe being vertically movable between a lower cuvette wash station probe position and an upper cuvette wash station probe position, the cuvette wash station being disposed such that the cuvette wash station probe is immediately above the cuvette washing site;

(r) a cuvette wash station probe positioning motor for moving the cuvette wash station probe between the lower cuvette was station probe position and the upper cuvette wash station probe position; and (s) cuvette wash station probe supply and disposal assembly for alternatively (1) providing pressurized washing liquid from a source of washing liquid to the cuvette wash station probe for washing a cuvette disposed within the random access analyzing station at the cuvette washing site and (2) providing a negative pressure to the internal chamber of the cuvette wash station probe for removing waste liquids from a cuvette disposed within the random access analyzing station at the analyzing site and for transferring such waste liquids to a disposal site.

2. A device for determining at least one parameter of a liquid comprising:

(a) a random access analyzing station sized and dimensioned to retain a plurality of cuvettes, and having an on-board control sample, the onboard control sample comprising a non-evaporating calibration standard material;

(b) at least one cuvette mixing site disposed proximate to the random access analyzing station;

(c) a random access analyzing station analyzing site disposed proximate to the random access analyzing station; and (d) an analyzer disposed proximate to the random access analyzing station analyzing site for determining at least one parameter of a liquid sample disposed within the cuvettes;

wherein the random access analyzing station is movable such that (i) the onboard control sample can be moved to and away from the random access analyzing station analyzing site, and (ii) individual cuvettes can alternatively be moved to and away from (1) the cuvette mixing site, (2) the cuvette washing site and (3) the random access analyzing station analyzing site.

3. The device of claim 1 wherein the onboard control sample is a gel.

4. The device of claim 3 wherein the control sample is a silicon gel.

5. The device of claim 4 wherein the index of refraction of the silicon gel is between about 1.3 ad about 1.5.

6. The device of claim 4 wherein an effective light scattering amount of inorganic particles are suspended within the silicon gel, the inorganic particles having an index of refraction greater than that of the silicon gel.

7. The device of claim 6 wherein the silicon gel is the result of the mixing and curing of a two-component system.

8. The device of claim 7 wherein one of the components has the composition comprising:

(1) 83 to 98.6 parts by weight of a silanol endstopped diorganopolysiloxane polymer, wherein the organo groups are monovalent hydrocarbon radicals, and (2) 1.4 to 17 parts by weight of resinous copolymer comprising $R_3SiO_{0.5}$ units and $SiO_2$ units, wherein R is a monovalent hydrocarbon radical and wherein said copolymer has from about 0.5 to about 1 $R_3SiO_{0.5}$ unit per $SiO_2$ unit.

9. The device of claim 7 wherein one of the components has the composition comprising:

(1) 10 to 50 parts by weight of an alkyl silicate of the formula

and partial hydrolysis products thereof, wherein $R^1$ and $R^2$ are monovalent hydrocarbon radicals, m is 0 or 1; and which is pre-reacted with (2) an effective catalytic amount of curing catalysts;

(3) 10 to 30 parts by weight of a self-bonding additive having the formula:

(3-a)

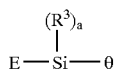

wherein $R^3$ is a monovalent hydrocarbon radical, E is a hydrolyzable group selected from the group consisting of alkoxy, phenoxy, amino and dialkylamino and θ is a nitrogen functional radical which is reacted with unsaturated or aromatic hydrocarbon residue, which in addition to nitrogen functionality may be functionalized by a radical selected from the group consisting of amino, cyano, thio, oxo and ester, and combinations thereof, and a is a number varying from 0 to 2; and (4) 10 to 40 parts by weight vinyl terminated linear diorganopolysiloxane fluid in a viscosity varying from 100 to 50,000 centipoise at 25° C., wherein the organo groups are monovalent hydrocarbon radicals.

10. The device of claim 2 wherein the onboard control sample is a gel.

11. The device of claim 10 wherein the control sample is a silicon gel.

12. The device of claim 11 wherein an effective light scattering amount of inorganic particles are suspended within the silicon gel, the inorganic particles having an index of refraction greater than that of the silicon gel.

13. The device of claim 13 wherein the silicon gel is the result of the mixing and curing of a two-component system.

14. The device of claim 14 wherein one of the components has the composition comprising:

(1) 83 to 98.6 parts by weight of a silanol endstopped diorganopolysiloxane polymer, wherein the organo groups are monovalent hydrocarbon radicals, and (2) 1.4 to 17 parts by weight of resinous copolymer comprising $R_3SiO_{0.5}$ units and $SiO_2$ units, wherein R is a monovalent hydrocarbon radical and wherein said copolymer has from about 0.5 to about 1 $R_3SiO_{0.5}$ unit per $SiO_2$ unit.

15. The device of claim 14 wherein one of the components has the composition comprising:

(1) 10 to 50 parts by weight of an alkyl silicate of the formula:

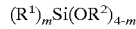

and partial hydrolysis products thereof, wherein $R^1$ and $R^2$ are monovalent hydrocarbon radicals, m is 0 or 1; and which is pre-reacted with (2) an effective catalytic amount of curing catalyst, (3) 10 to 30 parts by weight of a self-bonding additive having the formula (3-a)

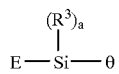

wherein $R^3$ is a monovalent hydrocarbon radical, E is a hydrolyzable group selected from the group consisting of alkoxy, phenoxy, amino and dialkylamino and θ is a nitrogen functional radical which is reacted with unsaturated or aromatic hydrocarbon residue, which in addition to nitrogen functionality may be functionalized by a radical selected from the group consisting of amino, cyano, thio, oxo and ester, and combinations thereof, and a is a number varying from 0 to 2; and (4) 10 to 40 parts by weight vinyl terminated linear diorganopolysiloxane fluid in a viscosity varying from 100 to 50,000 centipoise at 25° C., wherein the organo groups are monovalent hydrocarbon radicals.

* * * * *